United States Patent
Kim et al.

(10) Patent No.: US 11,648,524 B2
(45) Date of Patent: May 16, 2023

(54) METHOD FOR CONTROLLING ULTRAFAST CHEMICAL REACTION USING A MICROFLUIDIC REACTOR FABRICATED BY HIGH-RESOLUTION 3D METAL PRINTING TECHNIQUE

(71) Applicants: Postech Academy-Industry Foundation, Gyeongsangbuk-do (KR); Versitech Limited, Hong Kong (CN)

(72) Inventors: Dong Pyo Kim, Gyeongsangbuk-do (KR); Ji Tae Kim, Hong Kong (CN); Hyune Jea Lee, Seoul (KR)

(73) Assignees: POSTECH ACADEMY-INDUSTRY FOUNDATION, Pohang-si (KR); VERSITECH LIMITED, Hong Kong (CN)

( * ) Notice: Subject to any disclaimer, the term of this patent is extended or adjusted under 35 U.S.C. 154(b) by 0 days.

(21) Appl. No.: 17/387,932

(22) Filed: Jul. 28, 2021

(65) Prior Publication Data
US 2022/0032260 A1 Feb. 3, 2022

(30) Foreign Application Priority Data

Jul. 29, 2020 (KR) .................... 10-2020-0094380

(51) Int. Cl.
| | | |
|---|---|---|
| *B01J 19/00* | (2006.01) | |
| *C07F 7/22* | (2006.01) | |
| *B33Y 80/00* | (2015.01) | |
| *B33Y 70/00* | (2020.01) | |

(52) U.S. Cl.
CPC .......... *B01J 19/0093* (2013.01); *B33Y 80/00* (2014.12); *C07F 7/2208* (2013.01); *B01J 2219/00792* (2013.01); *B01J 2219/00822* (2013.01); *B01J 2219/00894* (2013.01); *B33Y 70/00* (2014.12)

(58) Field of Classification Search
CPC .... B01J 19/00; B01J 19/0093; B01J 2219/00; B01J 2219/00781; B01J 2219/00788; B01J 2219/00792; B01J 2219/00819; B01J 2219/00822; B01J 2219/00891; B01J 2219/00894; C07F 7/00; C07F 7/22; C07F 7/2208; C22C 33/00; C22C 33/02; C22C 33/0257; C22C 33/0278; C22C 33/0285
See application file for complete search history.

(56) References Cited

PUBLICATIONS

Kim et al., Submillisecond organic synthesis: Outpacing Fries rearrangement through microfluidic rapid mixing, May 2016, SCIENCE, vol. 352, Issue 6286, pp. 891-694. (Year: 2016).*
Kim et al., Harnessing [1,4], [1,5], and [1,6] Anionic Fries-type Rearrangements by Reaction-Time Control in Flow, 2017, Angew. Chem. Int. Ed., 56, 7863-7866. (Year: 2017).*
Gutmann et al., "Design and 3D printing of a stainless steel reactor for continuous difluoromethylations using fluoroform," React. Chem. Eng. (2017) 2:919-927.
Lee et al., "Enhanced Controllability of Fries Rearrangements Using High-Resolution 3D-Printed Metal Microreactor with Circular Channel," Small. (2019) 15(50):e1905005.

* cited by examiner

*Primary Examiner* — Natasha E Young
(74) *Attorney, Agent, or Firm* — Lex IP Meister, PLLC

(57) ABSTRACT

The present invention relates to a method for controlling an ultrafast chemical reaction using a microfluidic reactor, and more specifically, the present invention relates to a method for controlling an ultrafast chemical reaction such as the Fries rearrangement reaction and the like by using a microfluidic reactor by the 3D metal printing technique.

13 Claims, 4 Drawing Sheets

METHOD FOR CONTROLLING ULTRAFAST CHEMICAL REACTION USING A MICROFLUIDIC REACTOR FABRICATED BY HIGH-RESOLUTION 3D METAL PRINTING TECHNIQUE

CROSS-REFERENCE TO RELATED APPLICATION

This application claims priority to and the benefit of Korean Patent Application No. 10-2020-0094380, filed on Jul. 29, 2020, the disclosure of which is incorporated herein by reference in its entirety.

TECHNICAL FIELD

The present invention relates to a method for controlling an ultrafast chemical reaction using a microfluidic reactor, and more specifically, the present invention relates to a method for controlling an ultrafast chemical reaction such as the Fries rearrangement reaction and the like by using a microfluidic reactor fabricated by the high-resolution 3D metal printing technique.

BACKGROUND ART

The flow reaction system has been recognized as a useful platform for organic chemistry as well as pharmaceutical and chemical industries. These flow reaction systems with a high ratio of surface area to volume have unique features such as efficient transfers of heat and mass, enabling diverse green and sustainable chemical processes, and the precise control of reaction time is one of the most outstanding advantages of the flow-synthetic methods. Highly reactive chemicals that are impossible to handle in conventional batch reactors can be controlled by the precise adjustment of retention time in a flow reactor. In particular, it is highly striking to control ultrafast chemical reactions associated with highly short-lived unstable intermediates at high flow rates that can maximize the mixing efficiency at short time in the confined micro-reaction space. Moreover, the high flow rates may facilitate high throughput production for industrial applications.

Recently, the inventors of the present invention reported extremely rapid reactions, that is, the control of rapid intramolecular rearrangement through a newly designed microreactor with a small internal volume. The reactor is a polyimide (PI) film layered microfluidic device with high durability to chemicals and pressure, and it has been demonstrated to be capable of controlling molecular reaction times to sub-milliseconds. However, the use of metal devices may be much more desirable rather than the polymer material for the temperature control of highly sensitive intermediates as well as the durability of device. Furthermore, the laser ablation technique to fabricate the channel structure in PI film is limited to constituting only rectangular cross-sectional channels where the edges of the cross section cause a decrease in mixing efficiency. Thus, the complex mixing structure is required to increase the mixing efficiency in case of PI film-based devices, and in order to carry out ultrafast chemistry in a more effective manner, there is a need to study channel structures that can improve mixing efficiency in a small reaction volume.

RELATED ART DOCUMENTS

Non-Patent Documents (Non-Patent Document 1) *React. Chem. Eng.,* 2017, 2, 919-927. Design and 3D printing of a stainless steel reactor for continuous difluoromethylations using fluoroform.

DISCLOSURE

Technical Problem

The present invention provides a method for controlling the Fries rearrangement reaction using a microfluidic reactor by the 3D metal printing technique.

However, the technical problems to be achieved by the present invention are not limited to the aforementioned problem, and other problems which are not mentioned will be clearly understood by those skilled in the art from the following description.

Technical Solution

The present invention provides a method for controlling a chemical reaction using a microreactor. The microreactor may include a flow channel with a circular cross section.

The chemical reaction may be an ultrafast chemical reaction (or an ultrafast rearrangement reaction).

The ultrafast chemical reaction may be the Fries Rearrangements.

The flow channel may be formed such that the flow path for injecting a first fluid, the flow path for injecting a second fluid, and the merging path of the first fluid and the second fluid form a T shape.

The flow channel may be 3D printed, and may be produced by a selective laser melting (SLM) method.

The microreactor may be composed of a metal, and the metal may be stainless steel.

The ultrafast chemical reaction may use a compound of Chemical Formula 1 below as a starting material to obtain a compound of Chemical Formula 2a below.

[Chemical Formula 1]

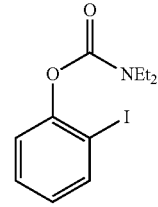

[Chemical Formula 2a]

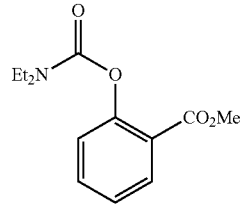

The ultrafast chemical reaction may use a compound of Chemical Formula 3 below to obtain a compound of Chemical Formula 4 below.

[Chemical Formula 3]

[Chemical Formula 4]

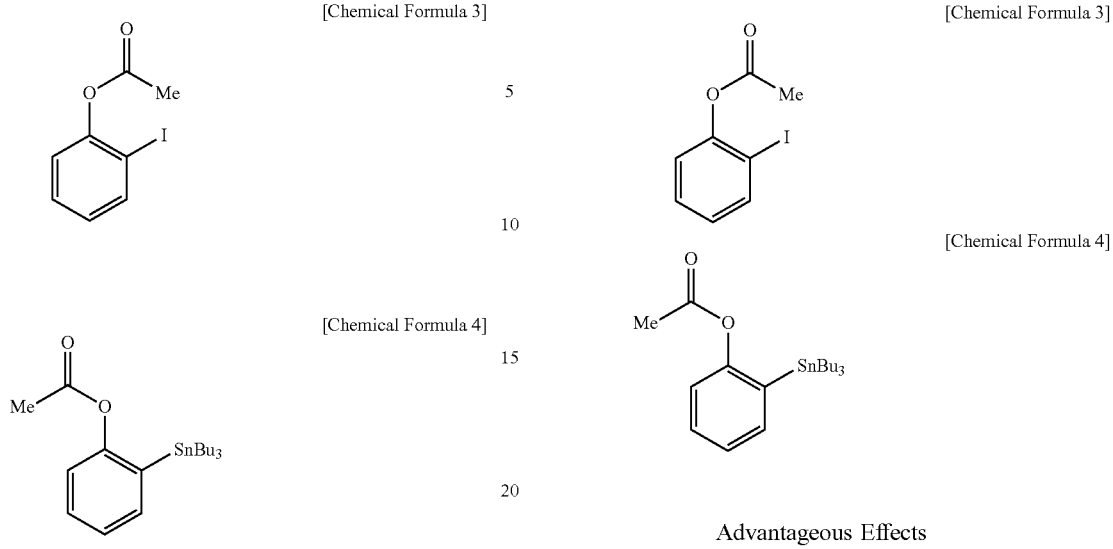

In addition, the present invention provides a microreactor for controlling an ultrafast chemical reaction (or an ultrafast rearrangement reaction), including a flow channel formed such that the flow path for injecting a first fluid, the flow path for injecting a second fluid, and the merging path of the first fluid and the second fluid form a T shape, wherein the flow channel has a circular cross section. The ultrafast chemical reaction may be the Fries Rearrangements.

In addition, the present invention provides a method for using a compound of Chemical Formula 1 below as a starting material to obtain a compound of Chemical Formula 2a below, by using a microreactor having a flow channel with a circular cross section.

[Chemical Formula 1]

[Chemical Formula 2a]

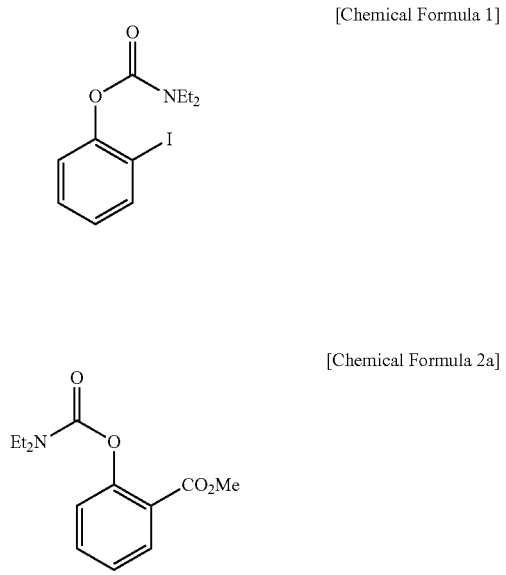

In addition, the present invention provides a method for using a compound of Chemical Formula 3 below as a starting material to obtain a compound of Chemical Formula 4 below, by using a microreactor having a flow channel with a circular cross section.

Advantageous Effects

According to the present invention, it is possible to easily control an ultrafast chemical reaction such as the Fries Rearrangements and the like by using a microreactor having a flow channel with a circular cross section.

DESCRIPTION OF DRAWINGS

FIG. 3a shows the CFD simulation of a channel structure and mixing efficiency at a reaction time of 333 μs, FIG. 3b shows an X-ray 2D image (scale bar: 1 mm), and FIG. 3c shows the 3D visualization image of an x-ray scan image.

MODES OF THE INVENTION

Figure 1A:
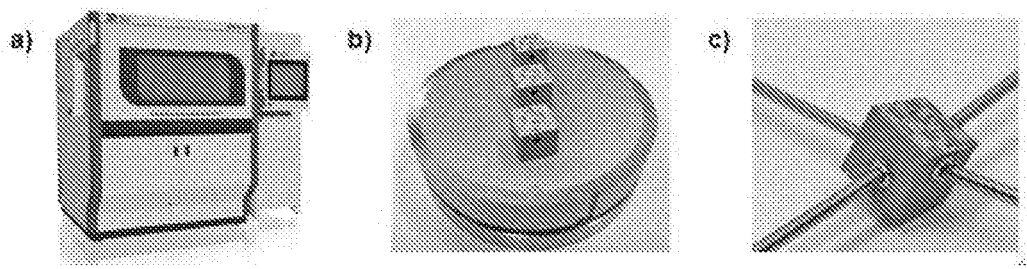
FIG. 1a is a schematic representation of the fabrication process of a micro (fine) fluidic reactor. a) 3D MicroPrint GmbH. b) After 3D printing, the printed structure is disassembled in the printer. c) Connection with an SUS tube by micro laser welding.

Hereinafter, the present invention will be described in more detail through exemplary embodiments. Objects, features and advantages of the present invention will be easily understood through the following exemplary embodiments. The present invention is not limited to the exemplary embodiments described herein and may be embodied in other forms. The exemplary embodiments introduced herein are provided so that the spirit of the present invention can be sufficiently conveyed to those of ordinary skill in the art to which the present invention pertains. Therefore, the present invention should not be limited by the following exemplary embodiments The present invention provides a method for enhancing the control of an ultrafast chemical reaction such as the anionic Fries rearrangement reaction and the like by using a three-dimensional printed stainless-steel microreactor (3D-PMR) having a circular-shaped cross-sectional fluid channel fabricated by a high-resolution selective laser melting (SML) method with a size of several tens of microns.

In the present specification, the ultrafast chemical reaction refers to an intramolecular rearrangement reaction by anions, and it specifically refers to the anionic Fries rearrangement reaction.

Hereinafter, the present invention will be described in more detail with reference to the drawings and examples.

Reagents: Tetrahydrofuran (THF, anhydrous), phenyllithium (PhLi) and diethyl ether ($Et_2O$, anhydrous) were purchased from Sigma-Aldrich. Unless otherwise mentioned, all commercial materials were used without further purification. All electrophiles were purchased from Sigma-Aldrich or TCI and used without further purification.

Device: The microfluidic device was fabricated by 3D MicroPrint GmbH (DMP 50 GP) in the SLM type. The microreactor was connected to a stainless-steel tube (SUS316, inner diameter of 1 mm), which was purchased from GL Science, by micro welding. A micro reactor system was constructed by cutting stainless steel to an appropriate length and connecting with a stainless-steel fitting (GL Science, 1/16" OUW).

Reaction procedure: The microfluidic system was immersed in a cooling bath to control the temperature. The reagents were continuously injected into the microfluidic system using syringe pumps (Harvard Model PHD 2000) equipped with syringes (gas tight syringes, 50 mL, inner diameter: 27.6 mm) purchased from SGE Analytical Science. Unless otherwise mentioned, after steady state was reached, the product solution was collected for 30 seconds.

Spectrometric identification: Nuclear magnetic resonance (NMR) spectra were recorded on Bruker Avance III (500 MHz for $^1H$ NMR and 125 MHz for $^{13}C$ NMR). Unless otherwise mentioned, $^1H$ and $^{13}C$ chemical shifts were recorded in the ppm down-field of $Me_3SiCl$ or $CHCl_3$ as a standard in $CDCl_3$. Low resolution mass spectra (LRMS) were recorded by Agilent 5975 VL MSD mass spectrometry (EI). The 3D X-ray scan images were obtained with Shimadzu/SMX-225CT (Regional Innovation Center for Next Generation Industrial Radiation Technology (Wonkwang University, Iksan, Korea)). The 3D visualization was performed with VGStudioMax 3.2 program.

Procedure of fabricating a microfluidic microreactor: Models were designed by CAD software program to fabricate three types of micro-open channel structures and 3D printed metal microreactors (3D-PMR) for resolution testing. Afterwards, the designed structures were then decomposed into a series of cross-sectional slices by the process software. The slices were printed layer-by-layer by fusion of metal powders. The structures were printed with the micro-laser sintering method system of 3D MicroPrint GmbH (DMP 50 GP) (a) of FIG. 1a). As the metal powders, 17-4PH chromium-nickel-copper alloyed stainless-steel powders with a <5 µm was used. The micro-SLM machine used an Ytterbium fiber laser at a maximum of 400 watts to fuse the stainless-steel powders when it scanned the build area. After a designated area of the layer was exposed, the build plate was lowered and another layer of powder was dispensed over an object. After the printing process, the printed structure was disassembled in the printer (b) of FIG. 1a), and sonication was performed for 3 hours to remove the remaining particles. Then, the inner diameter of a 1,000 µm stainless-steel tube (SUS 316, GL Science, 1/16") was connected with 3D-PMR by micro-laser welding (c) of FIG. 1a).

Hereinafter, the mixing efficiencies of various channel configurations in different designs were compared and experimentally verified. Ultrafast intramolecular rearrangement reactions were controlled by comparing high-resolution 3D-printed stainless-steel metal microreactors (3D-PMRs) with different cross-sectional geometries. Compared to a rectangular cross-sectional channel (250 µm×125 µm), 3D-PMR with circular channels showed enhanced controllability in the rapid Fries-type rearrangement reaction, due to the excellent mixing efficiency confirmed based on computational flow dynamics (CFD) simulations. Although very rapid intramolecular rearrangement of sterically small acetyl groups occurs at 333 µs of the reaction time, the desired intermolecular reaction may lead to high conversion and yield by using 3D-PMR. In addition, the T-shaped channel structure showed an excellent synthetic yield of unrearranged products at sub-milliseconds of the remaining time, which may allow easy stacking of channels for high-throughput production.

Figure 1B:
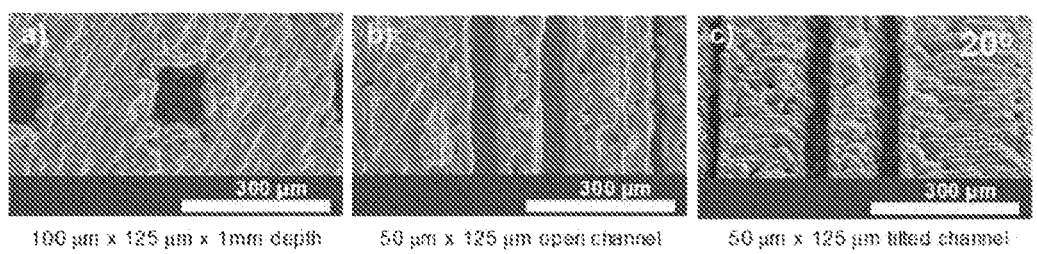
FIG. 1b shows SEM images of the inside of a 3D printed channel: a) A closed channel of 100 μm×125 μm×1 mm depth. b) An open rectangular channel of 50 μm×125 μm. c) A 20° tilted open rectangular channel of 50 μm×125 μm.

First, in order to demonstrate 3D printing feasibility, the spatial resolution of 3D SLM printing was tested through open and closed channels in various dimensions (FIG. 1b). SLM printing of microchannels was performed using a focused 1,064 nm-laser spot (diameter Ø≤30 µm) and ultra-fine stainless-steel powders (17-4PH chromium-nickel-copper alloy; D90=7 µm). The use of stainless steel may ensure excellent chemical/mechanical tolerances in high pressure and heat-transfer performances which are critical to the performance of the microreactor. a) of FIG. 1b shows the fabricated rectangular closed channel structure with a dimension of 100 µm×125 µm (width (W)×height (H)). The open rectangular channel having a width of 50 to 500 µm and a height of 125 µm was also successfully fabricated (b) of FIG. 1b). The rounded corners of the circular cross-sectional channel were easily fabricated using the fabrication method of rectangular channel structures with right angles. Layered patterns with progressively varying lengths promoted structuring without collapse during printing. According to this design rule, fabrication reliability was improved upon stacking the structures by tilting about 20° (c) of FIG. 1b).

Figure 2:
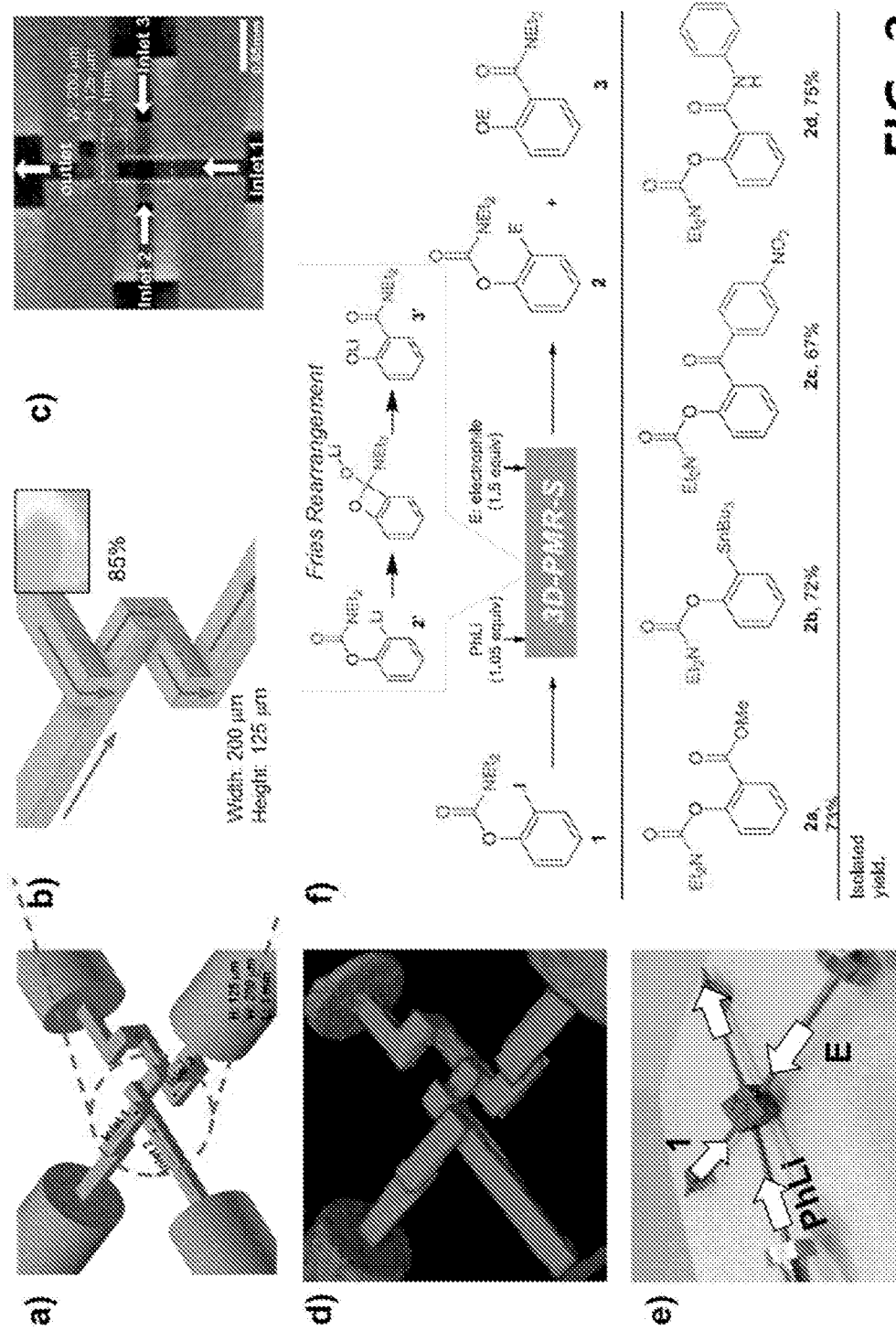
FIG. 2 schematically illustrates the fabrications of microfluidic devices and 3D-PMR-S, and their use for controlling the Fries rearrangement: a) A conceptual diagram of 3D-PMR-S with a five-turned serpentine rectangular channel including 3 inlets and 1 outlet. b) A conceptual diagram of CFD simulation of a mixing channel structure and mixing efficiency at a reaction time of 333 ρs. c) A captured X-ray scan 2D image of a fabricated monolithic cube (1 cm³), scale bar: 650 mm. d) A 3D visualization image obtained from X-ray image data. e) An optical image of 3D-PMR-S with an SUS capillary microreactor connected by laser micro-welding. f) Control of the Fries Rearrangements with various electrophiles using 3D-PMR-S.

According to the high-resolution 3D printing possibility, a microfluidic device was fabricated including a serpentine-type mixing channel (3D-PMR-S) with an internal volume of 25 nL to achieve a reaction time of 333 µs when the flow rate was maintained at 4.5 mL/min (a) of FIG. 2). The five-turned serpentine structural channel with a rectangular cross section (3D-PMR-S, width=200 µm, height=125 µm and total length=1 mm) was constructed, which is the same fluidic structure of the reported PI film chip microreactor. The printed channel structure was embedded inside a monolithic body of metal cube (1 cm³). The internal microchannel structure as a flow path in the opaque metal microreactor was fully inspected by 3D visualization using X-ray CT scans (c) and d) of FIG. 2). These resulting images indicate that the printed channels were completely continuous without significant defects, and their size and geometry were well matched to the initial design. Three inlets and a single outlet of the printed microreactor were connected to 1/16" stainless steel tubing by micro-welding (e) of FIG. 2). Then, the utility of 3D-PMR-S was used to control the anionic Fries rearrangement reaction (f) of FIG. 2). This device was used to demonstrate the performance of controlling the intramolecular Fries rearrangement as a model reaction of ultrafast chemistry.

A two-step intramolecular reaction was conducted by employing the same residence time of 333 μs in R1. All of 3 DPMRs were reactors having 3 inlets and 1 outlet, and these were structures in which inflow products which were flown from inlets 1 and 2 were mixed, and after passing through the pipe, these met an inflow product which was flown from inlet 3 to exit through the outlet, and in this case, the channel space, which was before inflow products which were flown from inlets 1 and 2 were mixed to meet an inflow product which was flown from inlet 3, corresponds to R1. For example, it refers to a reaction space in which substance (1) meets with PhLi before meeting another electrophile. For the control of the Fries-type rearrangement (unwanted movement of a carbamoyl group) in o-iodophenyl diethyl carbamate (1) for intermolecular capture reactions with various electrophiles at 25° C., efficient mixing and short residence times are important. The inventors of the present invention were able to obtain an unrearranged target product in high yield (67% or more) without a rearranged product related to intermediate 3'. This experiment showed that 3D-PMR-S can control ultrafast chemical reactions with similar performance as PI film chip microreactors.

Figure 3A:
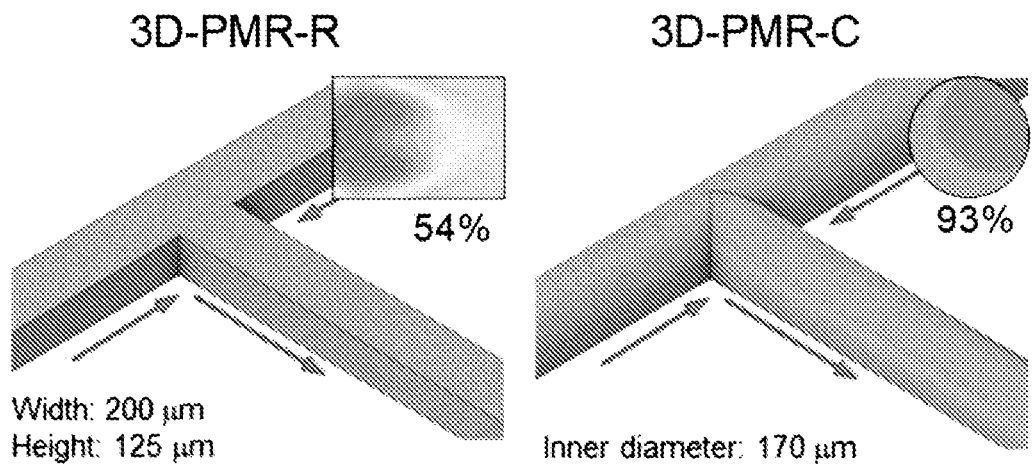
FIGS. 3a to 3c are conceptual diagrams and actual images of microfluidic devices with simple T-shaped channels and other cross-sectional geometry: 3D-PMR-R (T-shaped rectangular structure) and 3D-PMR-C (T-shaped circular structure). Specifically.
Figure 3B:
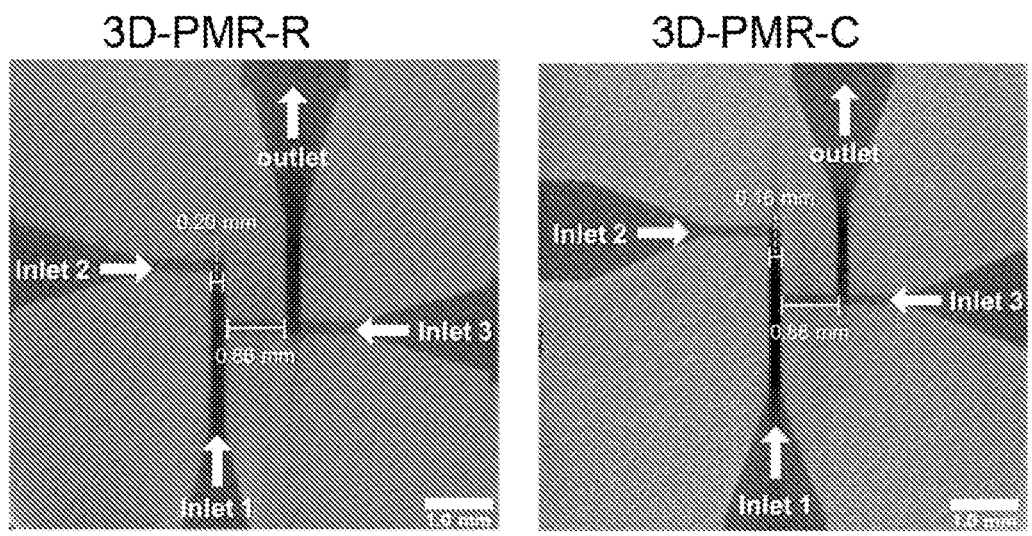

Next, in order to devise the microreactor with enhanced mixing efficiency and low inner pressure, computational flow dynamics (CFD) simulation was conducted. The mixing efficiencies of the additional two microchannels and the 3D-PMR-S microchannel were calculated: 1) a T-shaped microchannel with a rectangular cross section (3D-PMR-R); and 2) a T-shaped microchannel with a circular cross section (3D-PMR-C; FIG. 3a). The degree of mixing for the three types of channels with the same length (1 mm) and volume (25 nL) was estimated at different cut planes along the flow path from the initial mixing point. The CFD results indicated that the serpentine channel structure enhanced the mixing efficiency by increasingly inducing chaotic advection along with the number of turns. In addition, it was confirmed that the mixing efficiency of the 3D-PMR-S reached to 85% (b) of FIG. 2), which was much higher than 54% of the 3D-PMR-R at a constant total flow rate of 4.5 mL/min (asymmetric flow of 3.5 and 1.0 mL/min: FIG. 3a). In addition, 3D-PMR-C with a T-shaped circular cross-sectional channel structure showed the highest mixing efficiency of 93%, confirming that the cross-sectional structure had a great influence on the mixing efficiency.

It is noteworthy that the absence of dead volume in the circular channel, unlike the rectangular channel, significantly improved the mixing efficiency even without a complex serpentine channel with multiple numbers of turn. Furthermore, the planar geometry of the channel structure may facilitate to number-up the microreactors in a space-saving manner for scale-up production of chemicals in a compact system.

Figure 3C:
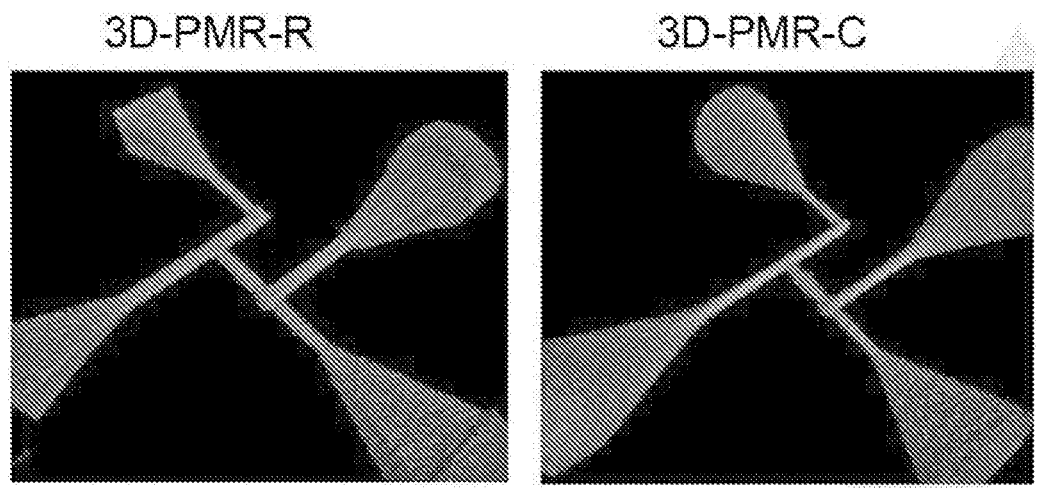

As shown in FIG. 3c, two microreactors with a circular cross-sectional channel structure (3D-PMR-C: diameter Ø=170 μm) and a simple rectangular channel structure (3D-PMR-R) were successfully fabricated by 3D SLM printing at sufficient precision. The 3D-PMR-R and 3D-PMR-C were connected with 1/16" of the stainless-steel tubes in the same method as 3D-PMR-S for the anionic Fries rearrangement reaction in Table 1.

TABLE 1

Comparative performance of anionic Fries rearrangement reactions in three types of 3D-printed metal microreactors with different channel geometry.

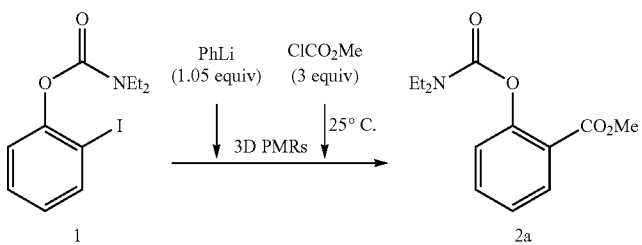

| Entry | 3D-PMRs | Mixing Efficiency [%] | Conversion [%][a] | Yield of 2a [%][a] |
|---|---|---|---|---|
| 1 | 3D-PMR-S | 85 | 74 | 73 |
| 2 | 3D-PMR-R | 54 | 49 | 48 |
| 3 | 3D-PMR-C | 93 | 87 | 85 |

[a] Determined by ¹H NMR spectroscopy using 1,3,5-trimethoxy benzene as an internal standard. The rearranged byproducts were not detected.

TABLE 2

Effect of mixing efficiency with the amount of PhLi

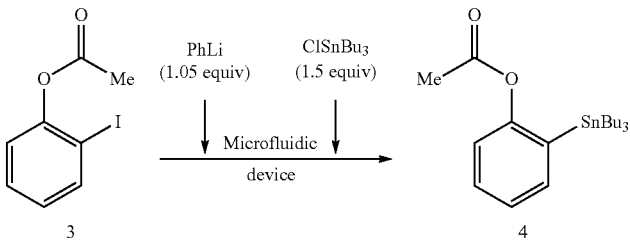

| Entry | Microfluidic device | Mixing Efficiency [%] | Equiv of PhLi | Yield of 4 [%][a] |
|---|---|---|---|---|
| 1 | 3D-PMR-S | 85 | 1.05 | 63 |
| 2 | 3D-PMR-S | 85 | 1.2 | 71 |
| 3 | 3D-PMR-C | 93 | 1.05 | 83 |
| 4 | 3D-PMR-C | 93 | 1.2 | 76 |

[a] Determined by $^1$H NMR spectroscopy using 1,3,5-trimethoxy benzene as an internal standard. The rearranged byproducts were not detected.

The conversion of starting compound 1 was significantly increased with the higher degree of mixing efficiency, leading to enhance the yield of compound 2a (Entries 1-3 and Table 1). The conversion was 74% when 3D-PMR-S was used. On the other hand, 49% and 87% of conversion could be achieved in 3D-PMR-R and 3D-PMR-C, respectively, without the formation of the carbamoyl-migrated byproduct. The results indicate that the small reaction volume gives a short residence time that generates high chemoselectivity, and that the high mixing efficiency generates the high conversion. Moreover, when an aryl compound bearing a sterically small acetyl group was used as a starting reagent, the effect of the used equivalents of PhLi was tested by using 3D-PMR-S and 3D-PMR-C microreactors (Table 2). The generated aryllithium intermediate was reacted with tributyltin chloride as an electrophile prior to the rearrangement. The 3D-PMR-C reactor showed a higher yield of compound 4 (yield of 83%) than the 3D-PMR-S reaction (yield of 71%) when the excess amount of PhLi was used (Entries 2 and 3), indicating that the mixing efficiency in 3D-PMR-C was higher than in 3D-PMR-S. Moreover, the yield of 3D-PMR-C was decreased upon the excess use of PhLi, which is contrast to the performance in 3D-PMR-S (Entries 1 and 2 vs Entries 3 and 4). The excess amount of PhLi helped to increase the conversion when the mixing efficiency was insufficient (Entries 1 and 2), while the over-equivalent PhLi could react with the fully transformed aryllithium intermediates under sufficiently efficient mixing to generate a byproduct, and thereby decreased the yield (Entries 3 and 4). Therefore, it is plausible that the advanced microfluidic device with improved mixing efficiency, such as 3D-PMR-C, led to a more excellent effect than the PI chip microreactor in controlling the intramolecular rearrangement of ultrafast chemistry.

In conclusion, the inventors of the present invention fabricated the high-resolution 3D-printed metal microfluidic device with high mixing efficiency for the precise control of rapid Fries-type rearrangements. Three types of novel metal microreactors were successfully fabricated by using the high-resolution 3D SLM printing method to achieve a short mixing time and a short residence time, which enabled the control of rapid reactions to give a high product yield by suppressing side reactions. Among three types of the devices, a simple designed T-shaped 3D-PMR-C reactor with the circular channel enabled superior control of the rearrangement to give the intramolecularly reacted product in high yield, compared to a complex designed 3D-PMR-S microreactor, even in the control of rapid migration of a sterically less-hindered acetyl group. Therefore, according to the present invention, it is possible to achieve high-throughput production of chemicals through ultrafast synthetic chemistry using a 3D printed microreactor having simply parallelized fluidic channels with excellent mixing efficiency.

PREPARATION EXAMPLE

Preparation of 2-iodophenyl diethylcarbamate (1): diethyl carbamoyl chloride (4.1 g, 30 mmol, 1.2 equiv.) was added dropwise to a solution of 2-iodophenol (5.5 g, 25 mmol) and potassium carbonate (10.2 g 73.8 mmol, 3.0 equiv.) in acetonitrile (50 mL) at room temperature. This mixture was refluxed at 90° C. in an oil bath. After stirring for 2 hours, the oil bath was removed, and it was filtered through a Kiriyama separation funnel, and a white solid was isolated and washed with ethyl acetate. The mixed filtrate was concentrated, and the formed crude product was purified by column chromatography (hexane/EtOAc=10:1 to 3:1) to obtain colorless oil of 2-iodophenyl diethylcarbamate (7.8 g, 24.4 mmol, 99%). $^1$H NMR (500 MHz, CDCl$_3$): δ 7.80 (dd, J=7.8, 1.6 Hz, 1H), 7.34 (td. J=7.8, 1.6 Hz, 1H), 7.19 (dd, J=7.8, 1.6 Hz, 1H), 6.93 (td, J=7.8, 1.6 Hz, 1H), 3.53 (q, J=7.1 Hz, 2H), 3.40 (q, J=7.1 Hz, 2H), 1.33 (t, J=7.1 Hz, 3H)), 1.23 (t, J=7.1 Hz, 3H) ppm. $^{13}$C NMR (125 MHz, CDCl$_3$): δ 152.8, 151.6, 139.0, 129.1, 126.8, 123.2, 90.7, 42.2, 41.9, 14.3, 13.2 ppm.

Preparation of 2-iodophenyl acetate (3): acetic anhydride (2.8 mL, 30 mmol, 1.2 equiv.) was added dropwise to a solution of 2-iodophenol (5.5 g, 25 mmol) and triethylamine (5.2 mL, 37.6 mmol, 1.5 equiv.) in dichloromethane (50 mL), and the mixture was stirred at 0° C. in an ice bath. After stirring for 30 minutes, the ice bath was removed, and the solution was stirred at room temperature overnight, and then half-saturated NH$_4$Cl (40 mL) was added. The organic phase was extracted with dichloromethane, dried in Na$_2$SO$_4$ and concentrated. The crude product was purified by column chromatography (hexane/EtoAc=10:1) to obtain 2-iodophenyl acetate (6.4 g, 24.3 mmol, 97%) as a light yellow liquid.

I-Li exchange reaction of 2-iodophenyl diethyl carbamate (1) and subsequent reaction with methyl chloroformate in 3D-PMR-S

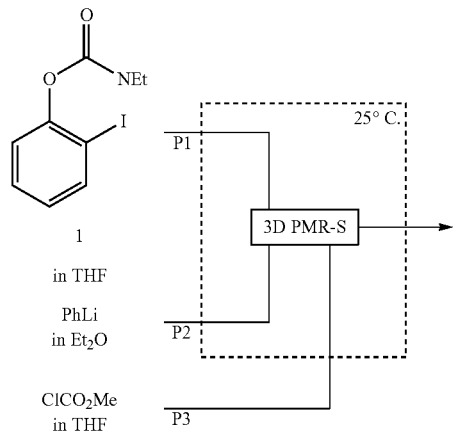

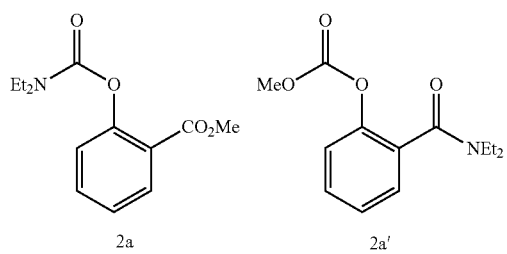

A microfluidic system which consisted of a 3D printed metal microreactor connected to a stainless-steel tube (inner diameter Ø: 1 mm, length: 5 cm) with pre-cooling stainless-steel tubes (P1, P2 and P3: inner diameter Ø: 1 mm, length: 50 cm) was used. A solution of 2-iodophenyl diethylcarbamate (1) (0.1 M in THF, 3.5 mL/min) and a solution of PhLi (0.368 M in diethyl ether, 1 mL/min) were introduced into two inlets of 3D-PMR using syringe pumps. The resulting solution was passed through a 1 mm mixing part and mixed with a solution of methyl chloroformate (0.6 M in THF, 1.75 mL/min). The resulting solution was passed through a tube microreactor (inner diameter Ø: 1 mm, length: 50 cm) connected to an outlet. After reaching steady state, the product solution was collected for 30 seconds while quenching with a saturated NH$_4$Cl aqueous solution (2 mL). Subsequently, diethyl ether (6 mL), brine (2 mL) and 1,3,5-trimethoxybenzene (50 mg) were added, followed by concentrating an aliquot (2 mL) of the organic phase, and it was analyzed by $^1$H NMR spectroscopy and GCMS spectroscopy. The $^1$H NMR yields of 2a and 2a' were determined, based on the relative intensities of peaks at 3.85 ppm (3H of 2a), 3.87 ppm (3H of 2a') and 6.01 ppm (3H of 1,3,5-trimethoxybenzene).

I-Li exchange reaction of 2-iodophenyl diethylcarbamate (1) and subsequent reaction with various electrophiles in 3D-PMR-S

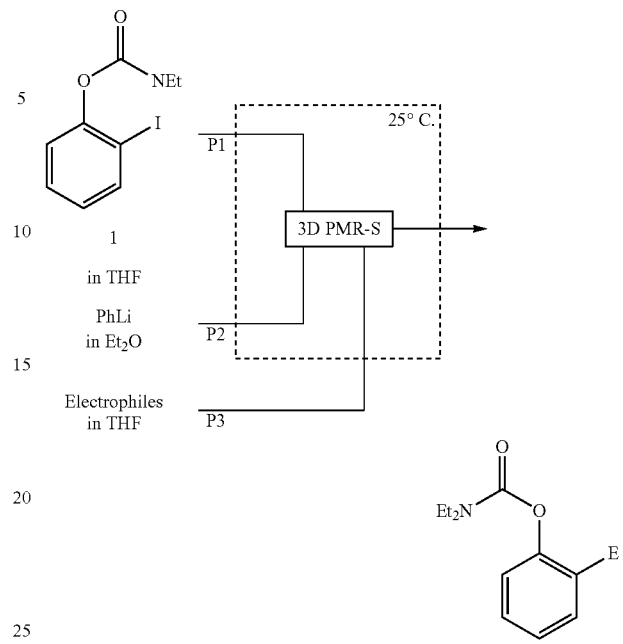

A microfluidic system which consisted of a 3D printed metal microreactor connected to a stainless-steel tube (inner diameter Ø: 1 mm, length: 5 cm) with pre-cooling stainless-steel tubes (P1, P2 and P3: inner diameter Ø: 1 mm, length: 50 cm) was used. A solution of 2-iodophenyl diethylcarbamate (1) (0.1 M in THF, 3.5 mL/min) and a solution of PhLi (0.368 M in diethyl ether, 1 mL/min) were introduced into two inlets of 3D-PMR-2 using syringe pumps. The resulting solution was passed through a 1 mm mixing part and mixed with an electrophile solution (0.3 M in THF, 1.75 mL/min). The resulting solution was passed through a tube microreactor (inner diameter Ø: 1 mm, length: 50 cm) connected to an outlet. After reaching steady state, the product solution was collected for 30 seconds while quenching with a saturated NH$_4$Cl aqueous solution (2 mL). For the syntheses of compounds 2b, 2c and 2d, chlorotributylstannane, 4-nitrobenzoyl chloride and phenylisocyanate were used as electrophiles in the reactions, respectively.

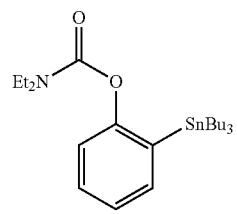

2-(Tributylstannyl)phenyl diethylcarbamate (2b)

Product 2b was obtained in a 72% isolated yield (60.7 mg). $^1$H NMR (500 MHz, CDCl$_3$) δ 7.36-7.34 (m, 1H), 7.26-7.23 (m, 1H), 7.10-7.07 (m, 1H), 6.99-6.97 (m, 1H), 3.38 (q, J=7.1 Hz, 2H), 3.32 (q, J=7.1 Hz, 2H), 1.47-1.41 (m, 6H), 1.29-1.11 (m, 12H), 0.99-0.96 (m, 6H), 0.80 (t, J=7.3 Hz, 9H) ppm. $^{13}$C NMR (125 MHz, CDCl$_3$): δ 156.7, 154.5, 136.9, 133.5, 129.4, 124.9, 121.5, 41.9, 41.6, 29.0, 27.4, 14.3, 13.6, 13.3, 9.7 ppm. LRMS (EI) for C$_{23}$H$_{41}$NO$_2$Sn m/z calculated value 482.29, measured value 482.0.

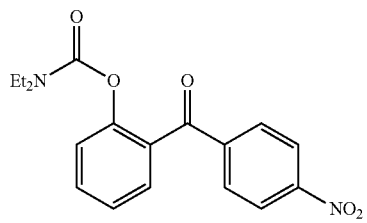

2-(4-Nitrobenzoyl)phenyl diethylcarbamate (2c)

Product 2c was obtained in a 67% isolated yield (40.1 mg). $^1$H NMR (500 MHz, CDCl$_3$) δ 8.20 (d, J=7.3 Hz, 2H), 7.90 (d, 7.3 Hz, 2H), 7.59 (td, J=7.8, 1.4 Hz, 1H), 7.42 (d, J=7.8 Hz, 1H), 7.24 (td, J=7.8, 1.4 Hz, 1H), 7.18 (d, J=7.8 Hz, 1H), 3.10 (q, J=7.2 Hz, 2H), 3.03 (q, J=7.2 Hz, 2H), 0.93 (m, 6H) ppm. $^{13}$C NMR (125 MHz, CDCl$_3$) δ 193.2, 153.0, 150.0, 149.6, 142.6, 132.8, 130.9, 130.7, 130.0, 125.1, 123.4, 123.3, 42.2, 41.7, 13.9, 13.1 ppm. LRMS for C$_{18}$H$_{18}$N$_2$O$_5$ (EI) m/z calculated value 342.35, measured value 342.0.

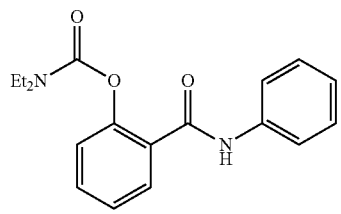

2-(Phenylcarbamoyl)phenyl diethylcarbamate (2d)

Product 2d was obtained in a 75% isolated yield (41.0 mg). $^1$H NMR (500 MHz, CDCl$_3$) δ 8.49 (br s, 1H), 7.68 (dd, J=7.7, 1.2 Hz, 1H), 7.54 (d, J=7.8 Hz, 2H), 7.41 (td, J=8.0, 1.7 Hz, 1H), 7.28-7.25 (m, 3H), 7.06-7.03 (m, 2H), 3.37-3.29 (m, 4H), 1.11-1.04 (m, 6H) ppm. $^{13}$C NMR (125 MHz, CDCl$_3$) δ 164.5, 154.9, 148.0, 138.2, 131.7, 131.0, 129.9, 129.0, 126.3, 124.3, 123.2, 119.5, 42.5, 42.2, 14.0, 13.2 ppm. LRMS (EI) for C$_{18}$H$_{20}$N$_2$O$_3$ m/z calculated value 312.36, measured value 312.0.

I-Li exchange reaction of 2-iodophenyl acetate (3) and subsequent reaction with chlorotributylstannane in 3D-PMR-C

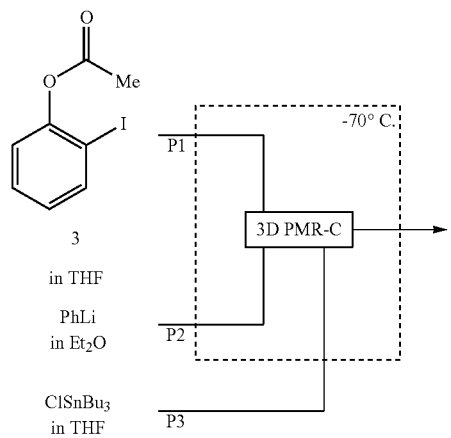

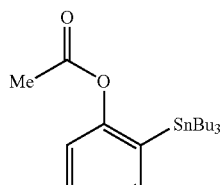

A microfluidic system which consisted of a 3D printed metal microreactor connected to a stainless-steel tube (inner diameter Ø: 1 mm, length: 5 cm) with pre-cooling stainless-steel tubes (P1, P2 and P3: inner diameter Ø: 1 mm, length: 50 cm) was used. A solution of 2-iodophenyl acetate (3) (0.1 M in THF, 3.5 mL/min) and a solution of PhLi (0.368 M in diethyl ether, 1 mL/min) were introduced into two inlets of 3D-PMR-3 using syringe pumps. The resulting solution was passed through a 1 mm mixing part and mixed with an electrophile solution (0.3 M in THF, 1.75 mL/min). The resulting solution was passed through a tube microreactor (inner diameter Ø: 1 mm, length: 50 cm) connected to an outlet. After reaching steady state, the product solution was collected for 30 seconds while quenching with a saturated NH$_4$Cl aqueous solution (2 mL). The $^1$H NMR yields of 3 and 4 were determined, based on the relative intensities of peaks at 2.37 ppm (3H of 3), 2.29 ppm (3H of 4) and 6.01 ppm (1,3,5-trimethoxybenzene).

The invention claimed is:

1. A method for controlling a chemical reaction using a microreactor having a flow channel with a circular cross section, wherein the flow channel is produced by a selective laser melting (SLM) method.

2. The method of claim 1, wherein the chemical reaction is an ultrafast chemical reaction.

3. The method of claim 2, wherein the ultrafast chemical reaction is the Fries Rearrangements.

4. The method of claim 1, wherein the flow channel is formed such that a flow path for injecting a first fluid, a flow path for injecting a second fluid, and a merging path of the first fluid and the second fluid form a T shape.

5. The method of claim 1, wherein the flow channel is 3D printed.

6. The method of claim 1, wherein the microreactor is composed of a metal.

7. The method of claim 6, wherein the metal is stainless steel.

8. The method of claim 1, wherein the chemical reaction uses a compound of Chemical Formula 1 below as a starting material to obtain a compound of Chemical Formula 2a below

[Chemical Formula 1]

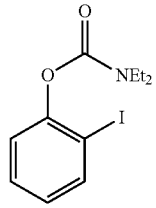

-continued

[Chemical Formula 2a]

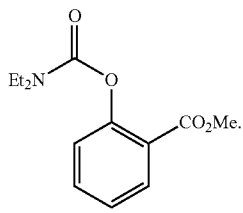

9. The method of claim 1, wherein the chemical reaction uses a compound of Chemical Formula 3 below to obtain a compound of Chemical Formula 4 below

[Chemical Formula 3]

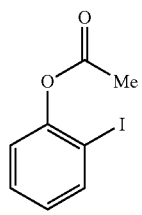

[Chemical Formula 4]

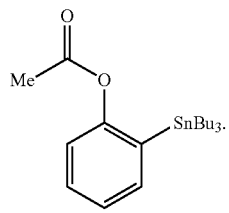

10. A microreactor for controlling an ultrafast chemical reaction of sub-millisecond, comprising a flow channel formed such that a flow path for injecting a first fluid, a flow path for injecting a second fluid, and a merging path of the first fluid and the second fluid form a T shape, wherein the flow channel has a circular cross section with a diameter of 170 μm, and the flow channel is produced by a selective laser melting (SLM) method.

11. The microreactor of claim 10, wherein the ultrafast chemical reaction of sub-millisecond is the Fries Rearrangements.

12. A method for using a compound of Chemical Formula 1 below as a starting material to obtain a compound of Chemical Formula 2a below, by using a microreactor having a flow channel with a circular cross section, wherein the flow channel is produced by a selective laser melting (SLM) method

[Chemical Formula 1]

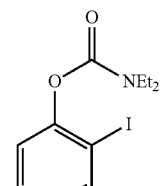

[Chemical Formula 2a]

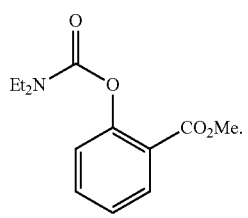

13. A method for using a compound of Chemical Formula 3 below as a starting material to obtain a compound of Chemical Formula 4 below, by using a microreactor having a flow channel with a circular cross section, wherein the flow channel is produced by a selective laser melting (SLM) method

[Chemical Formula 3]

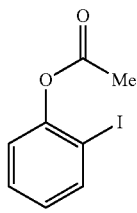

[Chemical Formula 4]

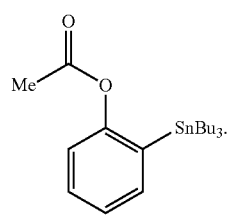

* * * * *